United States Patent [19]

Owens et al.

[11] Patent Number: 4,986,830
[45] Date of Patent: Jan. 22, 1991

[54] VALVULOPLASTY CATHETER WITH BALLOON WHICH REMAINS STABLE DURING INFLATION

[75] Inventors: Robert C. Owens, Forest Lake; Mark A. Rydell, Golden Valley, both of Minn.

[73] Assignee: Schneider (U.S.A.) Inc., Minneapolis, Minn.

[21] Appl. No.: 410,852

[22] Filed: Sep. 22, 1989

[51] Int. Cl.$^5$ ............................................. A61M 29/00
[52] U.S. Cl. ...................................... 606/194; 604/96
[58] Field of Search ................................. 604/96–101; 606/194; 600/29–31; 128/207.15

[56] References Cited

U.S. PATENT DOCUMENTS 4,327,736  5/1982  Inoue .................................... 604/101

Primary Examiner—Stephen C. Pellegrino
Assistant Examiner—William W. Lewis
Attorney, Agent, or Firm—Haugen and Nikolai

[57] ABSTRACT

A valvuloplasty catheter is described which includes an elongated flexible plastic tube dimensioned so as to allow it to be passed through the vascular system. Affixed to the distal end portion of the tube is an inflatable expander member which is intended to be positioned in the annulus of the valve to be treated. Inflation ports expose the interior of the expander member to the lumen of the tube so that when an inflation fluid is injected, under pressure, at the distal end of the tube, the expander member expands radially outward to spread the valve and free-up its leaflets. The novelty resides in providing first and second inflation ports of differing size so that the expander member inflates so as to create a dog-bone effect, tending to stabilize the expander member relative to the valve being treated.

4 Claims, 1 Drawing Sheet

4,986,830

VALVULOPLASTY CATHETER WITH BALLOON WHICH REMAINS STABLE DURING INFLATION

BACKGROUND OF THE INVENTION

I. Field of the Invention

This invention relates generally to catheters for facilitating the performance of transluminal valvuloplasty, and more particularly to the construction of such a catheter whereby the balloon or expander member is stabilized during the inflation thereof to inhibit movement of the balloon beyond the location of the valve being treated.

II. Discussion of the Prior Art

Between each atrium and ventricle of the heart, there is a somewhat constricted opening referred to as the atrioventricular orifice which is strengthened by fibrous rings and protected by valves. Also, the openings into the aorta and the pulmonary artery are also guarded by valves. More particularly, the orifice between the right ventricle and the pulmonary artery is guarded by the pulmonary valve and the orifice between the left ventricle and the aorta is guarded by the aortic valve. These two valves are called "semilunar valves" and consist of three semilunar cusps, each cusp being attached by its convex margin to the inside of the artery where it joins the ventricle, while its free border projects into the lumen of the vessel.

In the healthy heart, the semilunar valves offer no resistance to the passage of blood from the heart into the arteries as the free borders of the valve project into the arteries, but they form a complete barrier to the passage of blood in the opposite direction. In this case, each pocket becomes filled with blood, and the free borders are floated out and distended so that they meet in the center of the vessel. With age, however, the commissure lines defining the interface between the cusps can become calcified, inhibiting the ability of the valve to open and close in a normal fashion. In the past, such problems have been surgically addressed by opening the heart and repairing or replacing the valve with a man-made or animal replacement valve.

A more recent medical advance in the treatment of calcified coronary valves has involved the so-called transluminal valvuloplasty procedure in which, for example, in treating the aortic valve, a catheter is introduced into the femoral artery and advanced upward through the vascular system until it passes through the aorta to the site of the aortic semilunar valve. The catheter is equipped with a "balloon" near its distal end which is capable of being inflated to a predetermined maximum diameter by the introduction of an inflation fluid at the proximal end of the catheter structure. Expansion of the balloon while in the location of the valve is found to fracture the calcification, opening the commissure lines and again allowing the cusps to appropriately flex.

In some instances, it has been difficult to maintain the balloon at the desired position during the inflation thereof. Blood is inherently a slippery medium and as the inflation fluid is introduced into the balloon and it begins to swell, there is a tendency for the balloon to pop out of the valve site and, in some instances, it has been known to be projected with a sufficient force into the ventricle to perforate the ventricle near its apex, resulting in death.

In the Inoue U.S. Pat. No. 4,327,736, there is disclosed a balloon catheter especially designed for expanding a hollow organ and restoring resiliency to a theretofore stenosed structure. In accordance with the invention described therein, the balloon incorporates a non-extendable bag structure for defining the outer limit to which the balloon may be expanded. Surrounding the balloon are one or more elastic bands. When an inflation fluid is injected into the interior of the balloon to cause it to expand, the rubber bands cause the balloon to expand so as to create a dog-bone shape which tends to stabilize the balloon within the constriction being treated as expansion takes place.

OBJECTS

It is the principal object of the present invention to provide a transluminal valvuloplasty catheter with a provision for stabilizing the balloon during the inflation thereof to prevent it being forcibly propelled into the ventricular cavity or rearward back into the aorta.

SUMMARY OF THE INVENTION

In accordance with the present invention, the stabilization of the balloon during the inflation thereof in the course of a transluminal valvuloplasty procedure is achieved by providing an elongated flexible plastic tubular member which is dimensioned to pass through the vascular system. The tube includes at least two longitudinally spaced ports located on the distal end portion of the tube and which extend radially through the wall thereof to intersect with the lumen. The ports are of differing cross-sectional area. A tubular, inflatable expander member encircles the tube and overlies the two longitudinally spaced ports. The opposed ends of the expander member are bonded to the outer periphery of the tube. Means are provided at the proximal end of the tube for injecting an inflation fluid into the lumen such that when the expander member is constricted intermediate the longitudinally spaced ports, both ends of the expander member simultaneously inflate on either side of the constriction but at differing rates. By providing the larger port distally of the smaller one, it is insured that the expander member will have its distal end portion inflate before and at a greater rate than the proximal end portion. As such, by constraining, i.e., pulling back on the tubular member as the inflation fluid is injected, the expander member will be stabilized within the valve annulus.

DESCRIPTION OF THE PREFERRED EMBODIMENT

Figure 1:
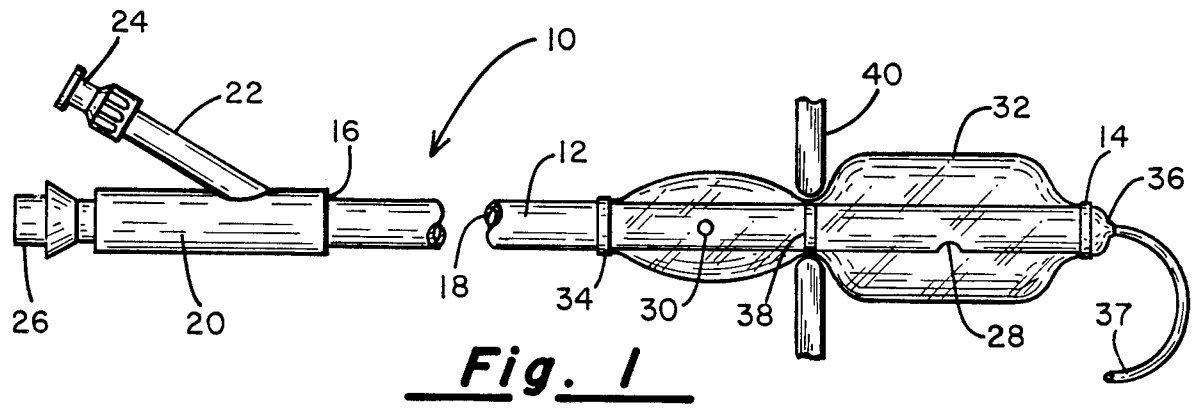
FIG. 1 is a partial side view of the valvuloplasty catheter at a preliminary stage of inflation.

Referring to FIG. 1, there is indicated generally by numeral 10 a valvuloplasty catheter constructed in accordance with the present invention. It is seen to comprise an elongated, flexible, plastic tube 12 having a distal end 14, a proximal end 16 and a lumen 18 running from the distal end to the proximal end. The catheter 12 may be fabricated from any number of materials commonly used in constructing intravascular catheters. Attached to the proximal end is a hub member 20 having an inflation fluid inlet port 22 integrally molded therewith and provided with a Luer fitting 24 to which an inflation syringe may be coupled. An inflation syringe suitable for the present application is disclosed in U.S. Pat. No. 4,723,938, which is assigned to the assignee of the instant invention. The catheter 10 may also include a guidewire port 26 formed on the proximal end portion of the hub 20.

Located a short distance, typically 10-40 mm, from the distal bond of the tube 12 is a first inflation port 28 depending upon balloon length. Then, a short distance proximal of the port 28 is a second inflation port 30. The ports 28 and 30 pass completely through the wall of the tube 12 so as to communicate with the lumen 18. The ports 28 and 30 are out of longitudinal alignment along the length of the catheter body, thus inhibiting any tendency for the tube to kink. It is also to be noted that the cross-sectional area of the port 28 is purposely made larger than that of the port 30. In a typical application, the port 28 may have a diameter of 0.5 mm while the port 30 may have a diameter of 2.0 mm. The expander member or balloon comprises a plastic film non-distensible sleeve 32 surrounding the distal end portion of the tube 12 in covering relation with respect to the inflation ports 28 and 30. The balloon 32 is bonded circumferentially at 34 and 36 to the exterior surface of the tube 12 to form a chamber which can be filled with an inflation fluid to expand it.

Balloon 32 is preferably fabricated from a biaxially oriented plastic material such as polyethylene terephthalate (PET). That material exhibits a high burst strength with relatively low extension when inflated to pressures in the range of from 3 to 10 atmospheres. While an expander member 32 fabricated from PET is highly suitable, it is not intended that the present invention be limited to that material. It is also contemplated that expandable films, such as polyethylene and silicone rubber may be used, especially if layered with fibers or the like to define a maximum outside diameter of the expander member when fully inflated.

Disposed between the two inflation ports 28 and 30 are one or more radiopaque marker bands 38. This allows the distal end portion of the catheter 10 to be precisely positioned relative to the aortic valve when viewed with a fluoroscope. In the drawings, the cardiac tissue of the valve ring is identified by numeral 40.

Figure 2:
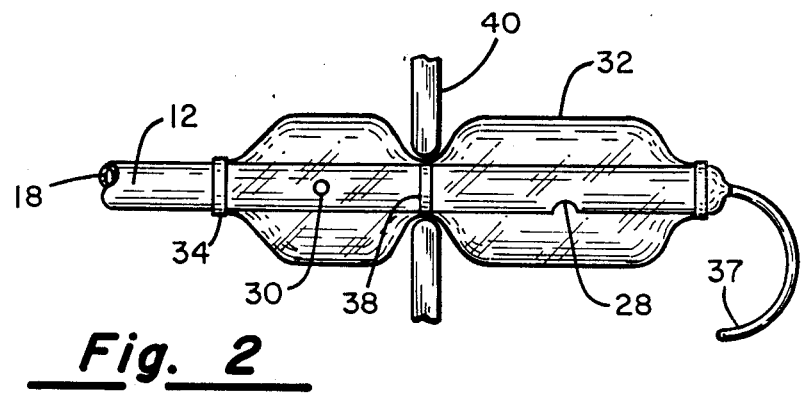
FIG. 2 is a partial side view of the valvuloplasty catheter at a later stage of inflation.

In accordance with the present invention, the valvuloplasty catheter is designed to remain stable within the heart valve being treated upon inflation. This result is achieved by providing inflation ports 28 and 30 of differing size, allowing the portions of the expander on opposed sides of the valvular restriction 40 to expand at different rates. In FIG. 1, the catheter 10 is illustrated as having been advanced through the vascular system with the balloon sleeve 32 uninflated and therefore collapsed against the exterior of the tube 12. When the marker bands 38 have been positioned relative to the valve 40 to be treated, an inflation fluid, typically a liquid contrast media, is injected through the inflation fluid inlet port 24 so that it flows through the lumen 18 of the tube 12 and simultaneously out the inflation ports 28 and 30. Because the more distal port 28 is of a larger size than the proximal port 30, the portion of the expander member 32 located distally of the constriction introduced by the presence of the valve 40 inflates at a greater rate than does the portion of the balloon 32 on the proximal side of the valve 40. As such, by applying tension to the proximal end 16 of the catheter as the inflation fluid is introduced, any tendency for the catheter to be propelled in the distal direction, i.e., pop out of the valve, is offset. As can be seen from FIG. 2, as the inflation fluid continues to be injected and the pressure increases, the more proximal portion of the balloon will also expand, approaching its maximum diameter while the valve wall 40 continues to create a restriction. In this fashion, the catheter expander member 32 is stabilized against movement in either the proximal or the distal direction.

Figure 3:
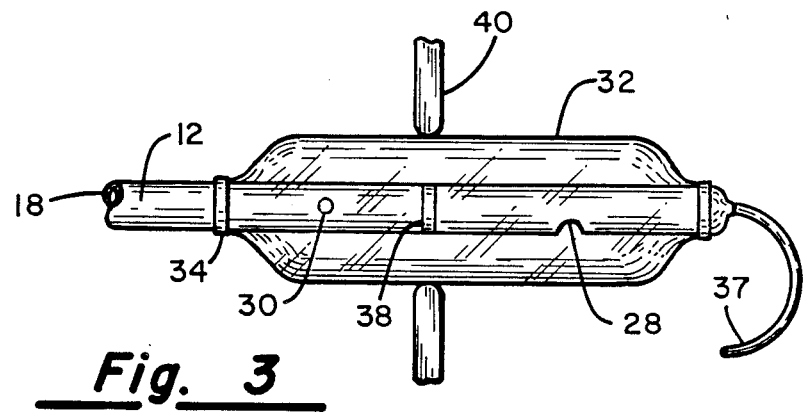
FIG. 3 is a partial cross-sectional view of the valvuloplasty catheter when fully inflated.

With reference next to FIG. 3, the pressure of the inflation fluid will be increased to its desired operating limit, and in doing so, will force open the valve 40 to separate any stenotic buildup of tissue over the commissures, thereby restoring flexibility to the valve leaflets.

It can be seen, then that by causing the expander member 32 to inflate through two specifically sized ports, one at each end of the expander member, the valve itself constricts the balloon in its center while both ends thereof inflate in advance of full inflation of the center portion. This selective inflation thus helps to stabilize the catheter, holding it in place against the forces of blood flow. Further, by properly sizing the ports, with the distal port being somewhat larger than the more proximal port, the inflation fluid can be preferentially introduced into the distal end portion of the balloon first, allowing tension on the catheter shaft to also help to stabilize the balloon against translational movement as the fluid pressure is increased to the desired level for causing expansion of the stenosed valve.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A valvuloplasty catheter comprising:
   (a) an elongated flexible, plastic, tube having a proximal end and a distal end and a lumen extending from said proximal end to said distal end, said tube including at least two longitudinally spaced ports of differing cross-sectional areas extending radially through said tube and intersecting said lumen, said ports being disposed at the distal end portion of said tube;
   (b) a tubular inflatable expander member encircling said tube and overlaying said longitudinally spaced ports, said expander member being bonded circumferentially to said tube at opposed ends of said expander member; and
   (c) means for injecting an inflation fluid into said lumen at said proximal end such that when said expander member is constricted intermediate said longitudinally spaced ports, both ends of said expander member simultaneously inflate but at differing rates on either side of the constriction.

2. The valvuloplasty catheter as in claim 1 wherein the most distal of said ports is of a larger cross-sectional area than the more proximal port such that the portion of said expander member distal of said constriction expands at a rate greater than the portion of said expander member proximal of said constriction.

3. The valvuloplasty catheter as in claim 1 wherein said longitudinally spaced ports are not longitudinally aligned along the length of said tube.

4. The valvuloplasty catheter as in any of claims 1-3 and further including a radiopaque marker means disposed on said tube at a location intermediate said opposed ends of said expander member.

* * * * *